United States Patent
Suga et al.

(10) Patent No.: US 9,063,050 B2
(45) Date of Patent: Jun. 23, 2015

(54) WEATHERING TEST INSTRUMENT AND SOLID-STATE LIGHT-EMITTING DEVICE SYSTEM

(71) Applicant: SUGA TEST INSTRUMENTS CO., LTD., Tokyo (JP)

(72) Inventors: Shigeo Suga, Tokyo (JP); Kenji Nishiwada, Tokyo (JP)

(73) Assignee: SUGA TEST INSTRUMENTS CO., LTD., Tokyo (JP)

( * ) Notice: Subject to any disclaimer, the term of this patent is extended or adjusted under 35 U.S.C. 154(b) by 0 days.

(21) Appl. No.: 14/312,334

(22) Filed: Jun. 23, 2014

(65) Prior Publication Data

US 2015/0027242 A1    Jan. 29, 2015

(30) Foreign Application Priority Data

Jul. 26, 2013   (JP) ................................ 2013-156010

(51) Int. Cl.
*G01N 17/00*    (2006.01)

(52) U.S. Cl.
CPC ............ *G01N 17/004* (2013.01); *G01N 17/002* (2013.01)

(58) Field of Classification Search
CPC ... G01N 17/002; G01N 17/004; G01N 17/00; G01N 3/60; G01N 2203/0222
USPC ........................................................ 73/865.6
See application file for complete search history.

(56) References Cited

U.S. PATENT DOCUMENTS

| | | | | |
|---|---|---|---|---|
| 3,202,811 A | * | 8/1965 | Hall, Jr. ............................ | 362/2 |
| 3,996,494 A | * | 12/1976 | Suga .............................. | 315/151 |
| 4,957,011 A | * | 9/1990 | Huber et al. ................. | 73/865.6 |
| 4,968,143 A | * | 11/1990 | Weston ......................... | 356/328 |
| 5,138,892 A | * | 8/1992 | Suga ............................. | 73/865.6 |
| 5,206,518 A | | 4/1993 | Fedor et al. | |
| 5,220,840 A | * | 6/1993 | Neigoff et al. ............... | 73/865.6 |
| 6,626,052 B1 | * | 9/2003 | Martin et al. ................ | 73/865.6 |
| 6,946,652 B2 | * | 9/2005 | Rathod et al. .............. | 250/252.1 |

(Continued)

FOREIGN PATENT DOCUMENTS

| | | |
|---|---|---|
| EP | 2682737 A1 * | 1/2014 |
| JP | B2-3195078 | 8/2001 |

(Continued)

*Primary Examiner* — David A Rogers
(74) *Attorney, Agent, or Firm* — Oliff PLC (57) ABSTRACT

Provided is a weathering test instrument that includes: a light source section including a plurality of solid-state light-emitting elements, in which the solid-state light-emitting elements are different in kind from one another, and are configured to emit light beams having respective wavelength regions that are different from one another; a light receptor configured to receive the light beams radiated from the light source section individually for the respective wavelength regions; and a controller configured to control radiant intensities of the respective solid-state light-emitting elements individually, based on received light amounts for the respective wavelength regions derived from the light receptor, and thereby control irradiance at a sample surface for each of the wavelength regions to allow an accelerated test of a sample to be performed.

10 Claims, 7 Drawing Sheets

(56) References Cited

U.S. PATENT DOCUMENTS

| | | | |
|---|---|---|---|
| 7,038,196 B2 * | 5/2006 | Scott et al. | 250/252.1 |
| 7,353,722 B2 * | 4/2008 | Schonlein | 73/865.6 |
| 2002/0139928 A1 * | 10/2002 | Rathod et al. | 250/252.1 |
| 2004/0233520 A1 * | 11/2004 | Ketola et al. | 359/361 |
| 2005/0087768 A1 * | 4/2005 | March et al. | 257/200 |
| 2005/0167580 A1 * | 8/2005 | Scott et al. | 250/252.1 |
| 2006/0049360 A1 * | 3/2006 | Schoenlein et al. | 250/372 |
| 2006/0254372 A1 * | 11/2006 | Scott et al. | 73/865.6 |
| 2007/0034026 A1 * | 2/2007 | Maciver et al. | 73/865.6 |
| 2011/0079071 A1 * | 4/2011 | Schultz et al. | 73/1.01 |
| 2014/0027652 A1 * | 1/2014 | Rudolph et al. | 250/455.11 |

FOREIGN PATENT DOCUMENTS

| | | |
|---|---|---|
| JP | B2-3924592 | 6/2007 |
| JP | B1-3945784 | 7/2007 |
| JP | A-2008-026156 | 2/2008 |
| JP | A-2009-043987 | 2/2009 |
| JP | A-2011-258700 | 12/2011 |
| JP | A-2012-221838 | 11/2012 |
| WO | WO 0212127 A2 * | 2/2002 |

* cited by examiner

WEATHERING TEST INSTRUMENT AND SOLID-STATE LIGHT-EMITTING DEVICE SYSTEM

This application claims the benefit of Japanese Priority Patent Application JP2013-156010 filed on Jul. 26, 2013, the entire contents of which are incorporated herein by reference.

BACKGROUND

The invention relates to a solid-state light-emitting device system and a weathering test instrument each including a light source section having solid-state light-emitting elements.

A weathering test instrument is an apparatus that applies light radiated from a light source (an artificial light source) as a substitute for the sun onto various samples under promoted environmental conditions (under accelerated test environment) to thereby evaluate and determine (e.g., perform a weathering test) a factor such as a degree of deterioration of those samples (e.g., materials). For example, reference is made to Japanese Patent Nos. 3945784, 3924592, and 3195078.

In general, a typical weathering test instrument is provided with a xenon arc lamp, a sunshine carbon arc lamp, an ultraviolet carbon arc lamp, a metal halide lamp, a fluorescent lamp, or the like as a light source inside a test tank which is adjustable in factors such as temperature and humidity. Also, such a weathering test instrument is provided with an annular sample-fixing frame rotated around the light source, and the samples are attached to the sample-fixing frame, whereby a test that lasts from about several tens of hours to about several thousands of hours is continuously performed under the promoted environmental conditions described above.

SUMMARY

In general, improvement in user convenience has been demanded in the field of weathering test instruments. Such a demand also applies to devices and systems other than the weathering test instruments. What is therefore desired is to propose a technique that enables improvement in the user convenience.

It is desirable to provide a weathering test instrument and a solid-state light-emitting device system each capable of improving user convenience.

A weathering test instrument according to an embodiment of the invention includes: a light source section including a plurality of solid-state light-emitting elements, in which the solid-state light-emitting elements are different in kind from one another, and are configured to emit light beams having respective wavelength regions that are different from one another; a light receptor configured to receive the light beams radiated from the light source section individually for the respective wavelength regions; and a controller configured to control radiant intensities of the respective solid-state light-emitting elements individually, based on received light amounts for the respective wavelength regions derived from the light receptor, and thereby control irradiance at a sample surface for each of the wavelength regions to allow an accelerated test of a sample to be performed.

A solid-state light-emitting device system according to an embodiment of the invention includes: a light source section including a plurality of solid-state light-emitting elements, in which the solid-state light-emitting elements are different in kind from one another, and are configured to emit light beams having respective wavelength regions that are different from one another; a light receptor configured to receive the light beams radiated from the light source section individually for the respective wavelength regions; and a controller configured to control radiant intensities of the respective solid-state light-emitting elements individually, based on received light amounts for the respective wavelength regions derived from the light receptor, and thereby control irradiance at a sample surface for each of the wavelength regions to allow an accelerated test of a sample to be performed. The solid-state light-emitting device system is applied to a weathering test instrument.

As used herein, the terms "radiant intensity" and "irradiance" in each wavelength region are each intended to encompass a value of "0 (zero)", which definition also applies to the following description as well.

In the weathering test instrument and the solid-state light-emitting device system according to the above-described respective embodiments of the invention, the radiant intensities of the respective solid-state light-emitting elements, which are different in kind from one another, in the light source section are individually controlled, and thereby the irradiance at the sample surface is controlled for each of the wavelength regions to allow an accelerated test of the sample to be performed. Hence, unlike a case where a proportion of irradiance is fixed for each wavelength region, it is possible to adjust a spectral irradiance distribution freely. Also, the radiant intensities of the respective solid-state light-emitting elements are controlled on the basis of the received light amounts for the respective wavelength regions obtained by the light receptor. Thereby, a feedback control of the irradiance for each of the wavelength regions is made possible. Hence, it is possible to perform the control of the irradiance for each of the wavelength regions and its management and maintenance more accurately.

Advantageously, the controller may control the radiant intensities of the respective solid-state light-emitting elements individually based on the received light amounts, to allow a spectral irradiance distribution set in the light source section to be maintained. In this embodiment, a desired spectral irradiance distribution is thereby maintained, making it possible to achieve an intended test easily and to achieve further improvement in convenience.

Advantageously, the set spectral irradiance distribution may be indicative of illuminance that is substantially same between the wavelength regions. In this embodiment, unlike a case where a lamp or the like is used as a light source (a case where a light source is used in which an unique spectral irradiance distribution having different illuminances for respective wavelength regions is indicated), it is possible to eliminate an influence attributable to a difference in strength of illuminance in a spectral irradiance distribution of a light source in measuring deterioration of the sample, upon performing, for example, a spectral aging test. In other words, it is possible to limit degradation factors of the sample to a wavelength factor, and thereby to draw a distinction between the wavelength factor and an illuminance factor. Hence, it is possible to perform more accurate spectral aging test.

Advantageously, the set spectral irradiance distribution may be a distribution in which illuminance in each of the wavelength regions is larger than illuminance in each wavelength region in a spectral irradiance distribution of sunlight. In this embodiment, it is possible to further promote acceleration in performing a weathering test while making the distribution close to the spectral irradiance distribution of the sunlight.

Advantageously, the set spectral irradiance distribution may be a distribution in which illuminance in an ultraviolet region is larger relatively than illuminance in any other wavelength region in the wavelength regions. In this embodiment, the illuminance in the ultraviolet region is made relatively larger, making it possible to further promote acceleration in performing a weathering test.

Advantageously, the light receptor may include: one or more light-receiving elements; and a plurality of wavelength-selective transmission filters provided on a light-receiving surface side of the one or more light-receiving elements, in which the wavelength-selective transmission filters are different in kind from one another, and are configured to allow the light beams radiated from the light source section to be transmitted therethrough individually for the respective wavelength regions. Alternatively, the weathering test instrument may further include a diffraction grating configured to spectrally disperse the light beams radiated from the light source section for the respective wavelength regions, and the light receptor may receive the light beams spectrally dispersed by the diffraction grating to individually receive the light beams radiated from the light source section for the respective wavelength regions.

Advantageously, the controller may control one or more of: the number of the solid-state light-emitting elements to emit the light beams; an emission intensity of one or more of the solid-state light-emitting elements; and emission time of one or more of the solid-state light-emitting elements, to individually control the radiant intensities of the respective solid-state light-emitting elements.

Advantageously, each of the solid-state light-emitting elements may be, but not limited to, a light-emitting diode (LED), an organic electroluminescence (EL) element, a laser diode (LD), or any other suitable semiconductor light-emitting device.

The weathering test instrument or the solid-state light-emitting device system according to any of the above-described embodiments of the invention controls the radiant intensities of the respective solid-state light-emitting elements that are different in kind from one another individually, to so control the irradiance for each of the wavelength regions as to allow an accelerated test of a sample to be performed. Hence, it is possible to freely adjust the spectral irradiance distribution, and thereby to improve user convenience.

It is to be understood that both the foregoing general description and the following detailed description are exemplary, and are intended to provide further explanation of the invention as claimed.

BRIEF DESCRIPTION OF THE DRAWINGS

The accompanying drawings are included to provide a further understanding of the disclosure, and are incorporated in and constitute a part of this specification. The drawings illustrate embodiments and, together with the specification, serve to explain the principles of the invention.

DETAILED DESCRIPTION

Figure 1:
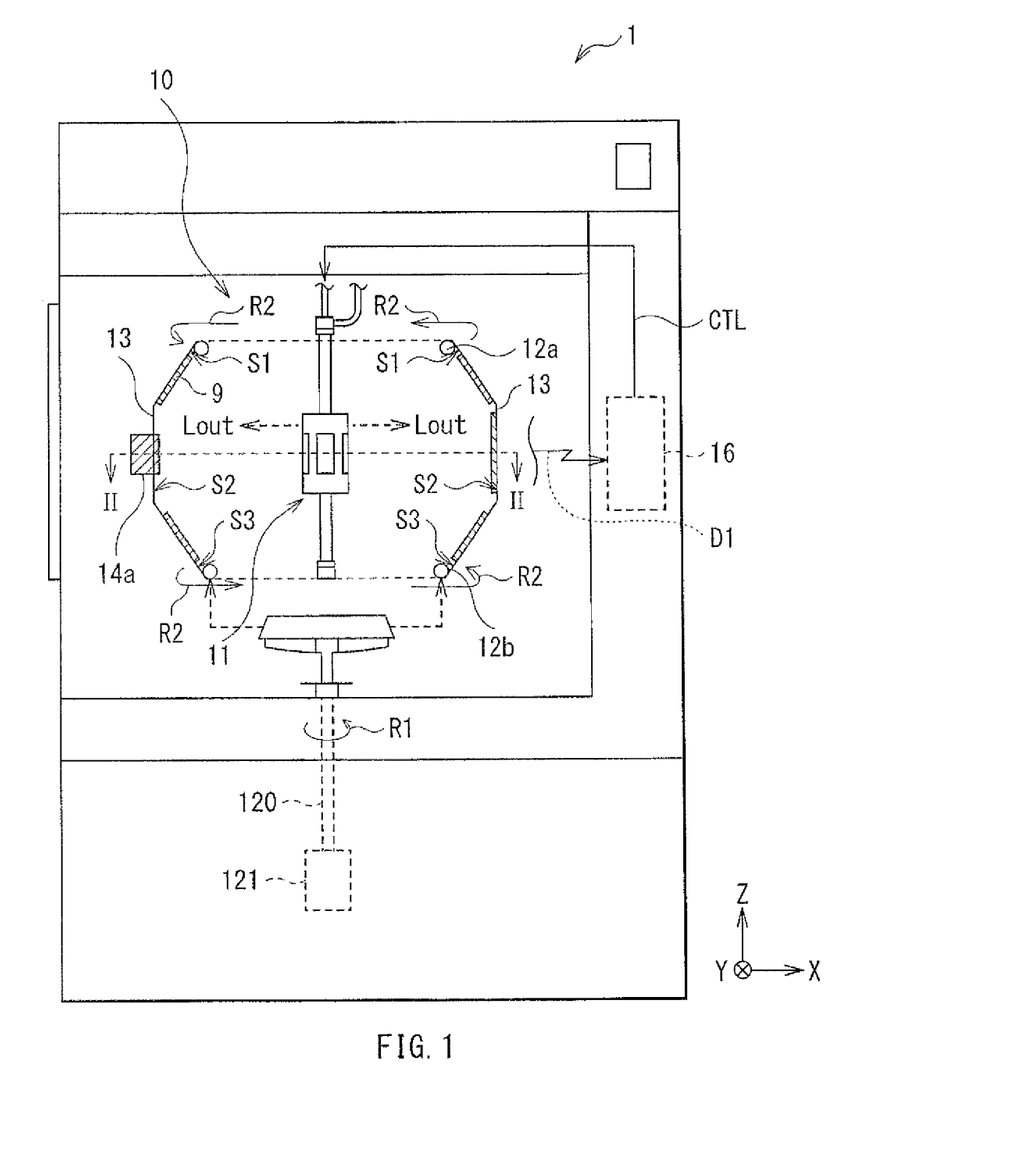
FIG. 1 schematically illustrates an example of an outline configuration of a weathering test instrument according to an embodiment of the invention.
Figure 2:
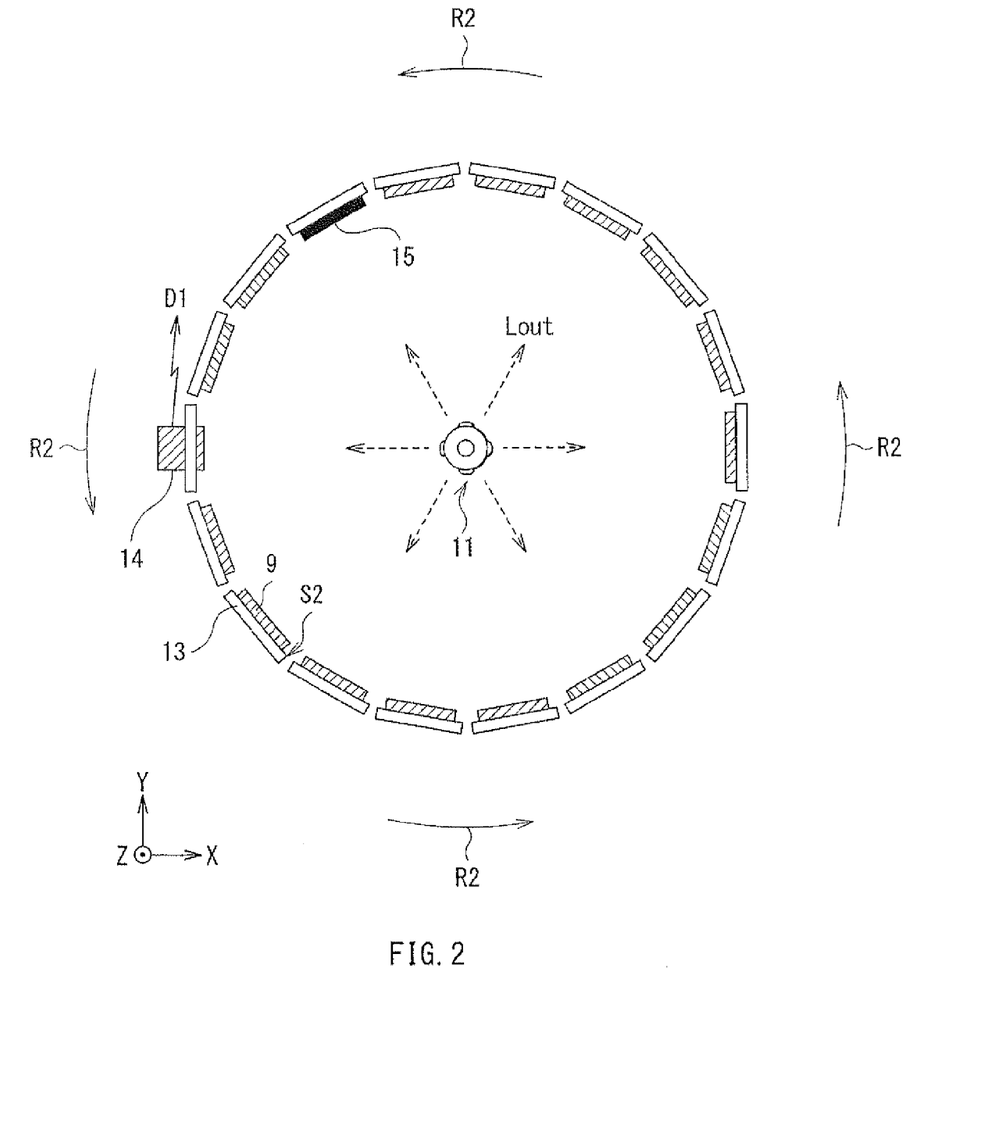
FIG. 2 schematically illustrates an example of a cross-sectional configuration as seen in an arrow direction and taken along line II-II denoted in FIG. 1.

In the following, some embodiments of the invention are described in detail with reference to the accompanying drawings, description of which is given in the following order.
1. Embodiment (an example of a weathering test instrument in which samples are rotated around a light source section)
2. Modifications
   First Modification (an example of a weathering test instrument (a spectral aging test instrument) in which a diffraction grating is used to spectrally disperse light)
   Second Modification (an example of a weathering test instrument (a spectral aging test instrument) in which whether to utilize the diffraction grating or not is switchable)
3. Other Modifications 1. Embodiment Configuration FIG. 1 schematically illustrates an example of an outline configuration of a weathering test instrument (weathering test instrument 1) according to an embodiment of the invention. FIG. 2 schematically illustrates an example of a configuration (an X-Y cross-sectional configuration) as seen in an arrow direction and taken along line II-II denoted in FIG. 1.

The weathering test instrument 1 is configured to perform a weathering test under promoted environmental conditions on samples (test pieces) 9 including various materials disposed inside a test tank 10. The weathering test instrument 1 may include, inside the test tank 10 which may be adjustable in factors such as temperature and humidity, a light source section 11, a pair of sample-fixing frames 12a and 12b, a plurality of sample holders 13, a light receptor 14, and a black panel thermometer 15. The weathering test instrument 1 may also include a rotary shaft 120, a slip ring 121, and a controller 16 as illustrated in FIG. 1. Among these elements, the light source section 11, the light receptor 14, and the controller 16 may correspond to a non-limiting example of a "solid-state light-emitting device system" according to one embodiment of the invention.

[Light Source Section 11]

The light source section 11 may be arranged near the center of the test tank 10 therein and provided on a support that extends in a Z-axis direction. The light source section 11 is configured to radiate radiant light Lout around (in an X-Y in-plane direction) a region within the test tank 10, as illustrated in FIGS. 1 and 2.

Figure 3A:
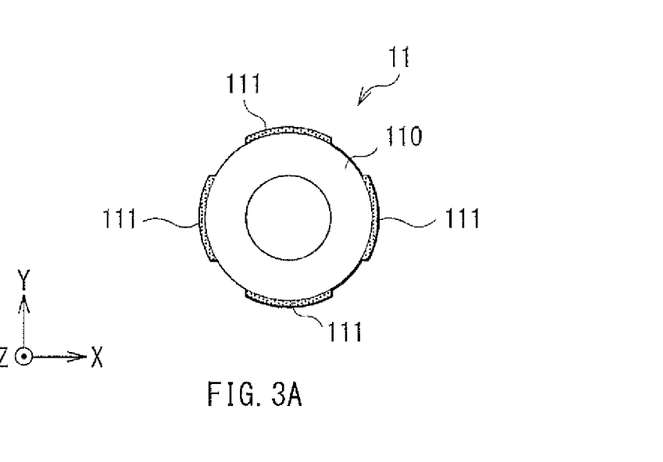
FIG. 3A is a cross-sectional view illustrating an example of a detailed configuration of a light source section illustrated in FIGS. 1 and 2.
Figure 3B:
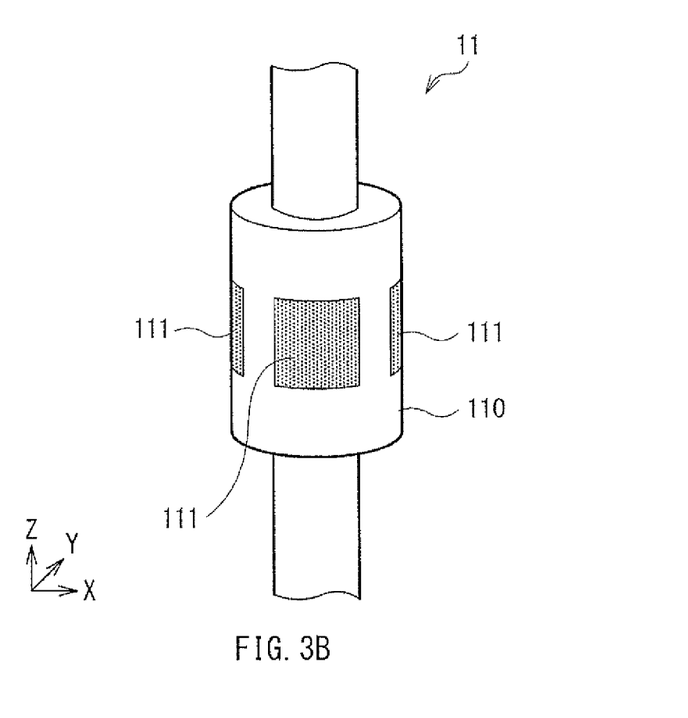
FIG. 3B is a perspective view illustrating the example of the detailed configuration of the light source section illustrated in FIGS. 1 and 2.

FIG. 3A illustrates an example of a detailed configuration of the light source section 11 in a cross-sectional (X-Y cross-sectional) view. FIG. 3B schematically illustrates the example of the detailed configuration of the light source section 11 illustrated in FIG. 3A in a perspective view.

Referring to FIGS. 3A and 3B, the light source section 11 may include: a columnar base 110 that extends in the Z-axis direction; and one or a plurality (four in the present embodiment) of light source packages 111 disposed around the base 110. For example, those four light source packages 111 may be rectangular, and so disposed side-by-side at predetermined intervals (at intervals that form 90 degree angles in the present embodiment) as to be located in a circle around the base 110.

Figure 4:
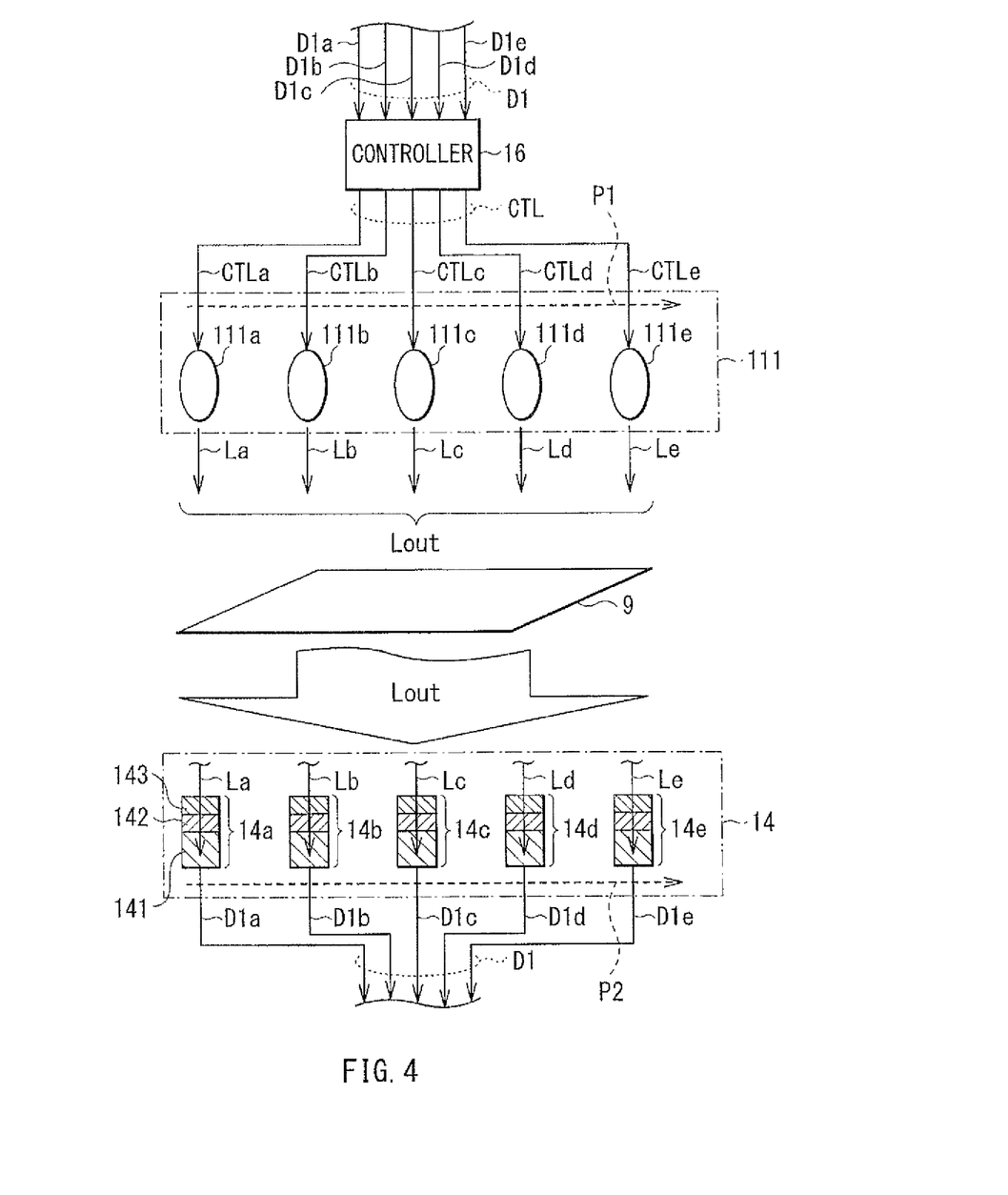
FIG. 4 is a schematic illustration for describing an outline of an example of control operation of the light source section using a light receptor and a controller.

As schematically illustrated in, for example, FIG. 4, each of the light source packages 111 includes a plurality of solid-state light-emitting elements 111a to 111e that are different in kind from one another (five kinds in the present embodiment) and configured to emit light beams having respective wavelength regions that are different from one another. For example, the solid-state light-emitting element 111a may emit radiant light (emission light) La having a wavelength region in a range from about 250 nm to about 350 nm, the solid-state light-emitting element 111b may emit radiant light Lb having a wavelength region in a range from about 350 nm to about 500 nm, and the solid-state light-emitting element 111c may emit radiant light Lc having a wavelength region in a range from about 500 nm to about 800 nm. Also, the solid-state light-emitting element 111d may emit radiant light Ld having a wavelength region in a range from about 800 nm to about 1000 nm, and the solid-state light-emitting element 111e may emit radiant light Le having a wavelength region in a range from about 1000 nm to about 1200 nm, for example. In the present embodiment, the solid-state light-emitting elements 111a to 111e may be arrayed in order from a short wavelength side to a long wavelength side in the radiant light emitted thereby, as denoted by an arrow P1 in FIG. 4. These pieces of radiant light La to Le are emitted, whereby the radiant light Lout is emitted from each of the light source packages 111 (the light source section 11) as illustrated in FIG. 4.

For example, the light-emitting elements 111a to 111e each may be, but not limited to, a light-emitting diode (LED), an organic electroluminescence (EL) element, a laser diode (LD), or any other suitable semiconductor light-emitting device. Also, light emission operations of those respective light-emitting elements 111a to 111e are controlled individually in accordance with a control signal CTL (control signals CTLa to CTLe) supplied from the controller 16 as described later.

The sample-fixing frames 12a and 12b illustrated in FIG. 1 may each be an annular frame so disposed in an X-Y plane that the light source section 11 is located at the center thereof. By rotation of the rotary shaft 120 in a rotation direction R1 as illustrated in FIG. 1, each of the sample-fixing frames 12a and 12b is configured to perform rotation operation at constant speed around the light source section 11 (serving as the center of rotation) in a rotation direction R2 that is in the same direction as the rotation direction R1. Thereby, each of the sample holders 13 to be described later is also configured to perform rotation operation in the rotation direction R2 around the light source section 11 as illustrated in FIG. 2.

The sample holders 13 are each so attached to the sample-fixing frames 12a and 12b as to connect the sample-fixing frame 12a to the sample-fixing frame 12b, and are attachable to and detachable from the sample-fixing frames 12a and 12b. Each of the sample holders 13 includes sample attachment surfaces S1 to S3 in this order from the sample-fixing frame 12a side to the sample-fixing frame 12b side. The sample attachment surfaces S1 to S3 face toward the light source section 11. As illustrated in FIG. 2, the sample 9 or the black panel thermometer 15 to be described later is arranged on each of the sample attachment surfaces S1 to S3. Such sample holders 13 as a whole may form a polygonal shape that corresponds to the number of those sample holders 13 in the X-Y plane as illustrated in FIG. 2, for example. In other words, the sample holders 13 are so arrayed on the sample-fixing frames 12a and 12b described above as to form a polygon thereon.

[Light Receptor 14]

The light receptor 14 (illuminometer) serves to measure irradiance of the radiant light Lout radiated from the light source section 11, and may be attached on the sample-fixing frames 12a and 12b as illustrated in FIGS. 1 and 2. For example, the light receptor 14 may be provided on the sample holder 13 to which no sample 9 is attached (no sample 9 is disposed) on the sample-fixing frames 12a and 12b. In the present embodiment, light reception data (light reception value) D1 obtained by the light receptor 14 may be sent to the later-described controller 16 through a wireless communication as illustrated in FIGS. 1 and 2.

The light receptor 14 is configured to receive the radiant light Lout derived from any of the light source packages 111 (the light source section 11) individually for each of the above-described wavelength regions. For example, as illustrated schematically in FIG. 4, the light receptor 14 may include a plurality of light-receiving sensors 14a to 14e that are different in kind from one another (five kinds in the present embodiment) and configured to receive the incident radiant light Lout for each of the wavelength regions. For example, the light-receiving sensor 14a may selectively receive the radiant light La having the wavelength region in a range from about 250 nm to about 350 nm, the light-receiving sensor 14b may selectively receive the radiant light Lb having the wavelength region in a range from about 350 nm to about 500 nm, and the light-receiving sensor 14c may selectively receive the radiant light Lc having the wavelength region in a range from about 500 nm to about 800 nm, in the incident radiant light Lout. Also, in the incident radiant light Lout, the light-receiving sensor 14d may selectively receive the radiant light Ld having the wavelength region in a range from about 800 nm to about 1000 nm, and the light-receiving sensor 14e may selectively receive the radiant light Le having the wavelength region in a range from about 1000 nm to about 1200 nm, for example. In the present embodiment, the light-receiving sensors 14a to 14e may be arrayed in order from a short wavelength side to a long wavelength side in the receivable radiant light, as denoted by an arrow P2 in FIG. 4.

The light-receiving sensors 14a to 14e each may have a stacked structure in which a light-receiving element (photoelectric conversion element) 141, a wavelength-selective transmission filter 142, and a diffuser 143 are laminated in this order from a backside to a light-receiving surface side, as illustrated in FIG. 4, for example. In this configuration, the diffusers 143 serve to diffuse the incident radiant light Lout within an incidence plane to cause a light intensity thereof to be uniform in plane. The wavelength-selective transmission filters 142 serve to allow the radiant light Lout derived from the light source section 11 to be transmitted therethrough individually for the respective wavelength regions. For example, the wavelength-selective transmission filter 142 in the light-receiving sensor 14a may allow the radiant light La having the wavelength region described above to be transmitted therethrough selectively, the wavelength-selective transmission filter 142 in the light-receiving sensor 14b may allow the radiant light Lb having the wavelength region described above to be transmitted therethrough selectively, and the wavelength-selective transmission filter 142 in the light-receiving sensor 14c may allow the radiant light Lc having the wavelength region described above to be transmitted therethrough selectively. Also, the wavelength-selective transmission filter 142 in the light-receiving sensor 14d may allow the radiant light Ld having the wavelength region described above to be transmitted therethrough selectively, and the wavelength-selective transmission filter 142 in the light-receiving sensor 14e may allow the radiant light Le having the wavelength region described above to be transmitted therethrough selectively, for example. Pieces of light reception data (light reception values) D1a to D1e output individually from the respective light-receiving sensors 14a to 14e are each supplied to the controller 16 as the above-described light reception data D1.

The black panel thermometer 15 is attached to any of the sample holders 13 (on any one of the sample attachment surfaces S1 to S3) as illustrated in FIG. 2, and serves as a thermometer for detecting temperature information of the samples 9. The temperature information may include a component indicative of light energy of the radiant light Lout in terms of temperature and a component indicative of environmental temperature in the test tank 10. The black panel thermometer 15 may include a thermosensitive body such as a bimetal, a platinum resistor, a thermistor, or a thermocouple, for example.

[Controller 16]

The controller 16 is configured to generate the control signal CTL on the basis of the light reception data D1 obtained by the light receptor 14, and control a radiant intensity of the light source section 11 (controls illuminance of the radiant light Lout) using the control signal CTL, as illustrated in FIGS. 1 and 4. For example, the controller 16 so controls discharge power of the light source section 11 as to allow a value (the irradiance) of the light reception data D1 to be substantially equal (desirably, equal) to a preset test condition value. Whereby, the controller 16 controls the irradiance applied to the sample 9 (a sample surface, or an irradiation surface) on the sample holder 13. Examples of a method of controlling such discharge power may include a PID (Proportional Integral Derivative) control, for example.

In the present embodiment, as illustrated in FIG. 4, the controller 16 is configured to control the radiant intensities of the respective solid-state light-emitting elements 111a to 111e that are different in kind from one another individually, and thereby, the controller 16 may control the irradiance at the sample 9 for each of the wavelength regions described above (for each of the pieces of radiant light La to Le), for example. Also, upon performing such control, the controller 16 controls the radiant intensities of the respective solid-state light-emitting elements 111a to 111e individually, based on the received light amounts (the values of the respective pieces of light reception data D1a to D1e) for the respective above-described wavelength regions obtained by the light receptor 14. For example, the controller 16 may be configured by a device such as a microcomputer. A control operation performed by the controller 16 is described later in greater detail.

[Function and Effect]

[A. Basic Operation]

In the weathering test instrument 1, the radiant light Lout is radiated within the test tank 10 from the light source section 11. Also, the sample-fixing frames 12a and 12b, to which the light receptor 14 and the sample holders 13 are attached, each perform the rotation operation around the light source section 11. Thereby, the sample 9 on each of the sample holders 13 is irradiated with the radiant light Lout. The successive application of the radiant light Lout, or the application based on a periodic (cyclic) operation that includes an irradiation period and a non-irradiation period, may be performed continuously throughout the predetermined test time (for example, from about several tens of hours to about several thousands of hours), whereby a weathering test is performed.

In such operation, the controller 16 generates the control signal CTL on the basis of the light reception data D1 obtained by the light receptor 14, and controls the radiant intensity of the light source section 11 using the control signal CTL to thereby control the irradiance applied to the sample 9. Thereby, the discharge power of the light source section 11 may be so controlled that the value of the light reception data D1 becomes substantially equal (desirably, equal) to the preset test condition value, ensuring stable operation of radiating the radiant light Lout.

[B. Control Operation of Radiant Intensity of Light Source Section 11]

Next, description is given in detail of the operation of controlling the radiant intensity of the light source section 11 (operation control of the irradiance applied to the sample 9) performed by the controller 16, with reference to FIGS. 4, 5A, 5B, and 5C.

First, in the present embodiment, the controller 16 controls the radiant intensities of the respective solid-state light-emitting elements 111a to 111e that are different in kind from one another individually, and thereby controls the irradiance at the sample 9 for each of the wavelength regions (for example, for each of the pieces of radiant light La to Le) as illustrated in FIG. 4. In such operation, the controller 16 may control one or more of: the number of solid-state light-emitting elements 111a to 111e to emit; an emission intensity of one or more of the solid-state light-emitting elements 111a to 111e; and emission time of one or more of the solid-state light-emitting elements 111a to 111e, to individually control the radiant intensities, for example.

In this manner, the radiant intensities of the respective solid-state light-emitting elements 111a to 111e, which are different in kind from one another, in the light source section 11 are individually controlled, and thereby the irradiance at the sample 9 is controlled for each of the wavelength regions. Hence, unlike a case where a proportion of irradiance is fixed for each wavelength region as in an example in which a lamp or the like is used as a light source, it is possible to adjust a spectral irradiance distribution at the sample 9 freely (in an optional fashion).

Also, in such operation, the controller 16 generates the control signals CTLa to CTLe on the basis of the received light amounts (the values of the respective pieces of light reception data D1a to D1e) for the respective above-described wavelength regions obtained by the light receptor 14, to individually control the radiant intensities of the respective solid-state light-emitting elements 111a to 111e that are different in kind from one another, as illustrated in FIG. 4. For example, the controller 16 may generate the control signal CTLa on the basis of the light reception data D1a on the radiant light La obtained from the light-receiving sensor 14a, to control the radiant intensity of the solid-state light-emitting element 111a. Also, the controller 16 may generate the control signal CTLb on the basis of the light reception data D1b on the radiant light Lb obtained from the light-receiving sensor 14b, to control the radiant intensity of the solid-state light-emitting element 111b. The controller 16 may generate the control signal CTLc on the basis of the light reception data D1c on the radiant light Lc obtained from the light-receiving sensor 14c, to control the radiant intensity of the solid-state light-emitting element 111c. The controller 16 may generate the control signal CTLd on the basis of the light reception data D1d on the radiant light Ld obtained from the light-receiving sensor 14d, to control the radiant intensity of the solid-state light-emitting element 111d. The controller 16 may generate the control signal CTLe on the basis of the light reception data D1e on the radiant light Le obtained from the light-receiving sensor 14e, to control the radiant intensity of the solid-state light-emitting element 111e.

In this manner, the control of the radiant intensities is performed on the basis of the received light amounts (the values of the respective pieces of light reception data D1a to D1e) for the respective wavelength regions obtained by the light receptor 14, allowing a feedback control of the irradiance for each of the wavelength regions to be performed. Hence, it is possible to perform the control of the irradiance for each of the wavelength regions and its management and maintenance more accurately.

Figure 5A:
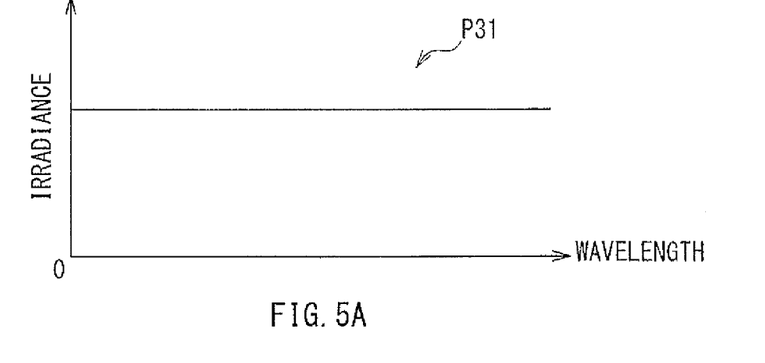
FIG. 5A schematically illustrates an example of a spectral irradiance distribution set in the light source section.
Figure 5B:
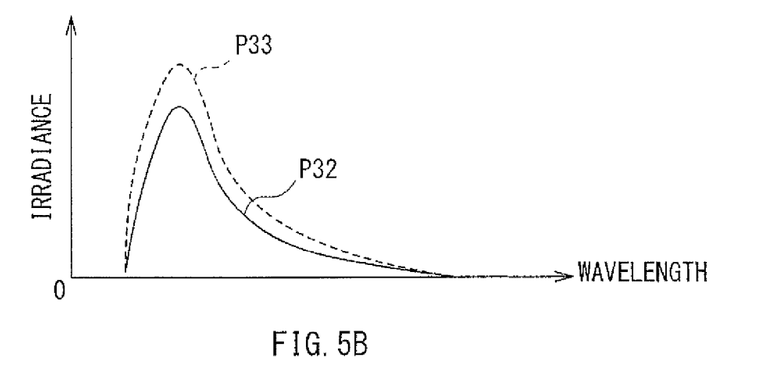
FIG. 5B schematically illustrates another example of the spectral irradiance distribution set in the light source section.
Figure 5C:
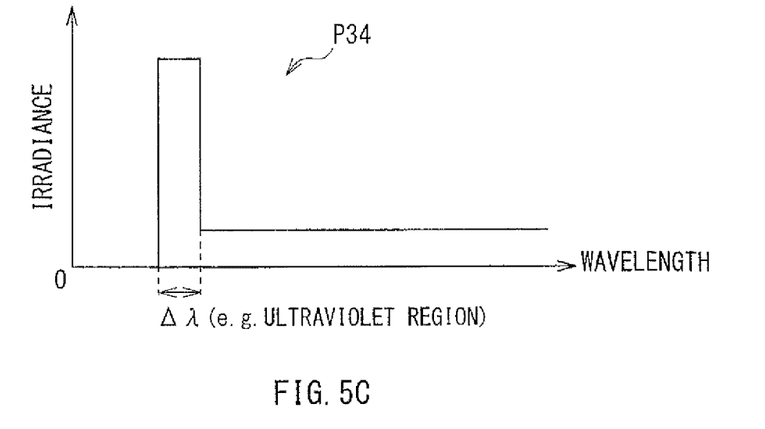
FIG. 5C schematically illustrates yet another example of the spectral irradiance distribution set in the light source section.

Further, the controller 16 may so individually control the radiant intensities of the respective solid-state light-emitting elements 111a to 111e, which are different in kind from one another, on the basis of the received light amounts described above as to maintain the spectral irradiance distribution set in the light source section 11 (as to keep the spectral irradiance distribution substantially constant and allow the same not to be varied), as illustrated in FIGS. 5A, 5B, and 5C, for example. Because a desired spectral irradiance distribution is thereby maintained, it is possible to achieve an intended test easily as described below, and to achieve further improvement in convenience.

FIG. 5A illustrates an example where the spectral irradiance distribution set in the light source section 11 (denoted by P31) is indicative of illuminance (irradiance) that is substantially the same (desirably, the same) between the wavelength regions. Utilizing such a spectral irradiance distribution is advantageous upon performing a spectral aging test as described, for example, in first and second modifications to be described later.

FIG. 5B illustrates an example where the spectral irradiance distribution set in the light source section 11 (denoted by P32 and P33) is a distribution close to a spectral irradiance distribution of sunlight. Utilizing such a spectral irradiance distribution makes it easier to reproduce the spectral irradiance distribution of the sunlight in a simple yet authentic way.

In particular, when the illuminance in each wavelength region in the set spectral irradiance distribution is made larger (for example, n-times larger where "n" is an integer of two or greater) than illuminance in each wavelength region in the spectral irradiance distribution of the sunlight as denoted by P33, it is advantageous in that acceleration in performing the weathering test is further promoted while making the distribution close to the spectral irradiance distribution of the sunlight.

Further, FIG. 5C illustrates an example where the spectral irradiance distribution set in the light source section 11 (denoted by P34) is a distribution in which the illuminance in a predetermined wavelength region $\Delta\lambda$ (an ultraviolet region in this example) is larger relatively than the illuminance in any other wavelength region in the wavelength regions. Because the illuminance in the ultraviolet region is made relatively larger in this example, utilizing such a spectral irradiance distribution further promotes acceleration in performing the weathering test. It is to be noted that the illuminance in any other wavelength region has a predetermined value greater than 0 (zero) in this example, it is not limited thereto. The illuminance in any other wavelength region may be set to zero.

In the present embodiment as described above, the radiant intensities of the respective solid-state light-emitting elements 111a to 111e that are different in kind from one another are controlled individually to control the irradiance at the sample 9 for each of the wavelength regions. Hence, it is possible to freely adjust the spectral irradiance distribution, and thereby to improve user convenience.

Also, such a control is performed based on the received light amounts (the values of the respective pieces of light reception data D1a to D1e) for the respective wavelength regions. Hence, it is possible to freely adjust the spectral irradiance distribution while utilizing a feedback control.

Further, because the solid-state light-emitting elements 111a to 111e are used as a light source in the light source section 11, it is also possible to achieve reduction in power consumption as compared with a case in which a lamp is used as a light source.

2. Modifications

Hereinafter, some modifications (first and second modifications) of the example embodiment described above are described. Note that the same or equivalent elements as those of the example embodiment described above are denoted with the same reference numerals, and will not be described in detail.

First Modification

Figure 6:
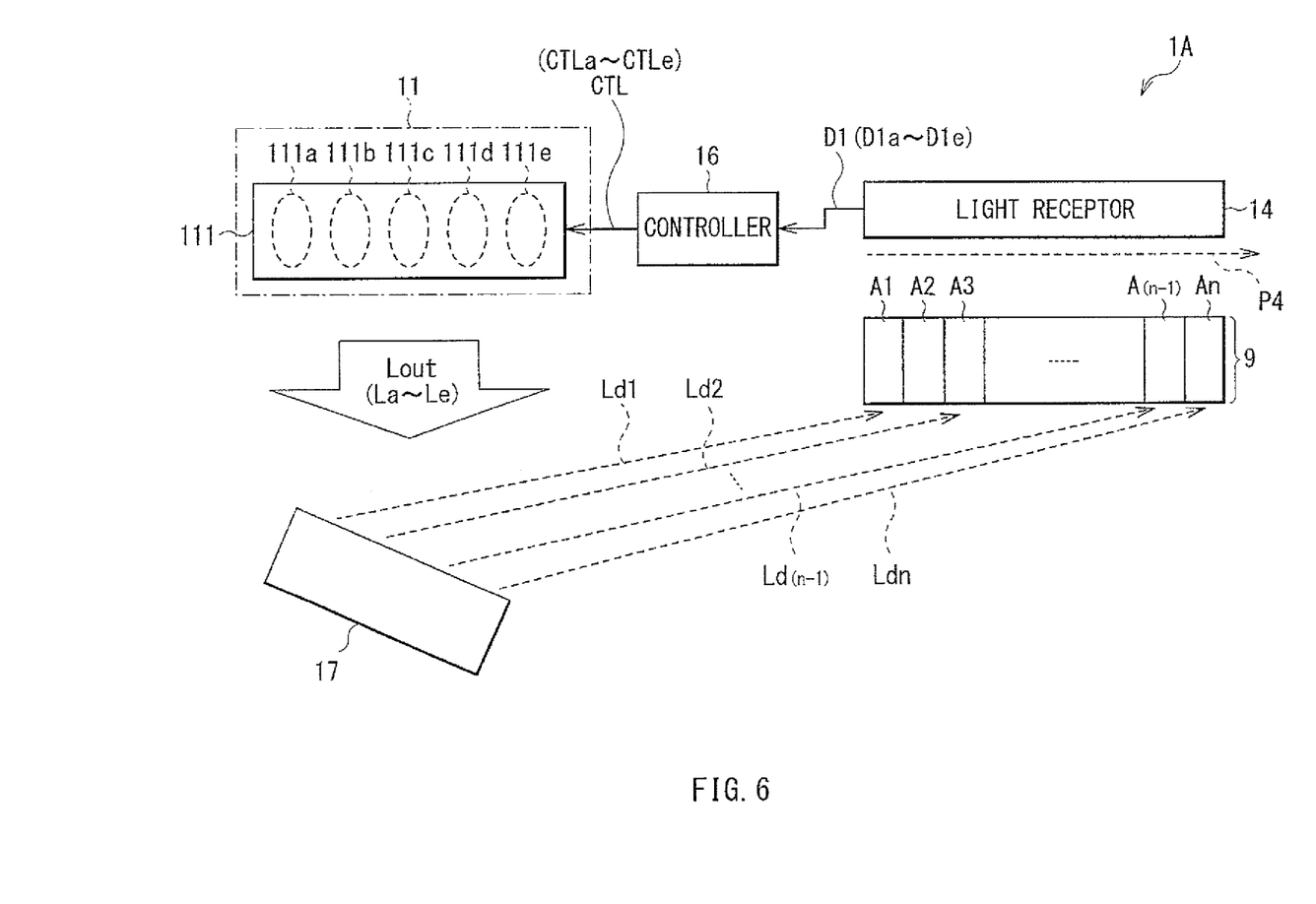
FIG. 6 schematically illustrates an example of an outline configuration of a weathering test instrument (a spectral aging test instrument) according to a first modification.

FIG. 6 schematically illustrates an example of an outline configuration of a weathering test instrument (a spectral aging test instrument) 1A according to a first modification. The spectral aging test instrument 1A serves to perform a test for measuring a degree of deterioration of the sample 9 for each wavelength region (performs a spectral aging test), and may include the light source section 11, a diffraction grating 17, a single sample holder (not illustrated) for fixing the sample 9, the light receptor 14, and the controller 16. The light source section 11 has the light source package 111 that includes the solid-state light-emitting elements 111a to 111e that are different in kind from one another as described above.

The diffraction grating 17 is configured to spectrally disperse the radiant light Lout (the pieces of radiant light La to Le) emitted from the light source section 11 (the light source package 111) for each of the wavelength regions, and allow spectrally-dispersed radiant light (pieces of diffracted light Ld1, Ld2, . . . , Ld(n−1), and Ldn) to exit therefrom to the sample 9.

The pieces of diffracted light Ld1 to Ldn thus exited the diffraction grating 17 are individually applied onto respective light reception regions A1, A2, A3, . . . , A(n−1), and An on a sample surface of the sample 9. Also, the light receptor 14 located near the sample 9 receives such pieces of diffracted light Ld1 to Ldn to receive the radiant light Lout for each of the wavelength regions. In the present modification, the respective pieces of diffracted light Ld1 to Ldn may be caused to be incident on the sample surface and the light receptor 14 in order from a short wavelength side to a long wavelength side as denoted by an arrow P4 in FIG. 6.

The present modification having the configuration described above achieves effects similar to those of the example embodiment described above, by virtue of functions similar to those of the above-described example embodiment basically.

Also, in the present modification, utilizing the spectral irradiance distribution illustrated, for example, in FIG. 5A as described above (the distribution indicative of illuminance that is substantially the same between the wavelength regions) also achieves the following effects. Namely, unlike a case where a lamp or the like is used as a light source (a case where a light source is used in which an unique spectral irradiance distribution having different illuminances for respective wavelength regions is indicated), it is possible to eliminate an influence attributable to a difference in strength of illuminance in a spectral irradiance distribution of a light source in measuring deterioration of the sample 9, upon performing the spectral aging test. In other words, it is possible to limit degradation factors of the sample 9 to a wavelength factor, and thereby to draw a distinction between the wavelength factor and an illuminance factor. Hence, it is possible to perform more accurate spectral aging test.

Second Modification

Figure 7:
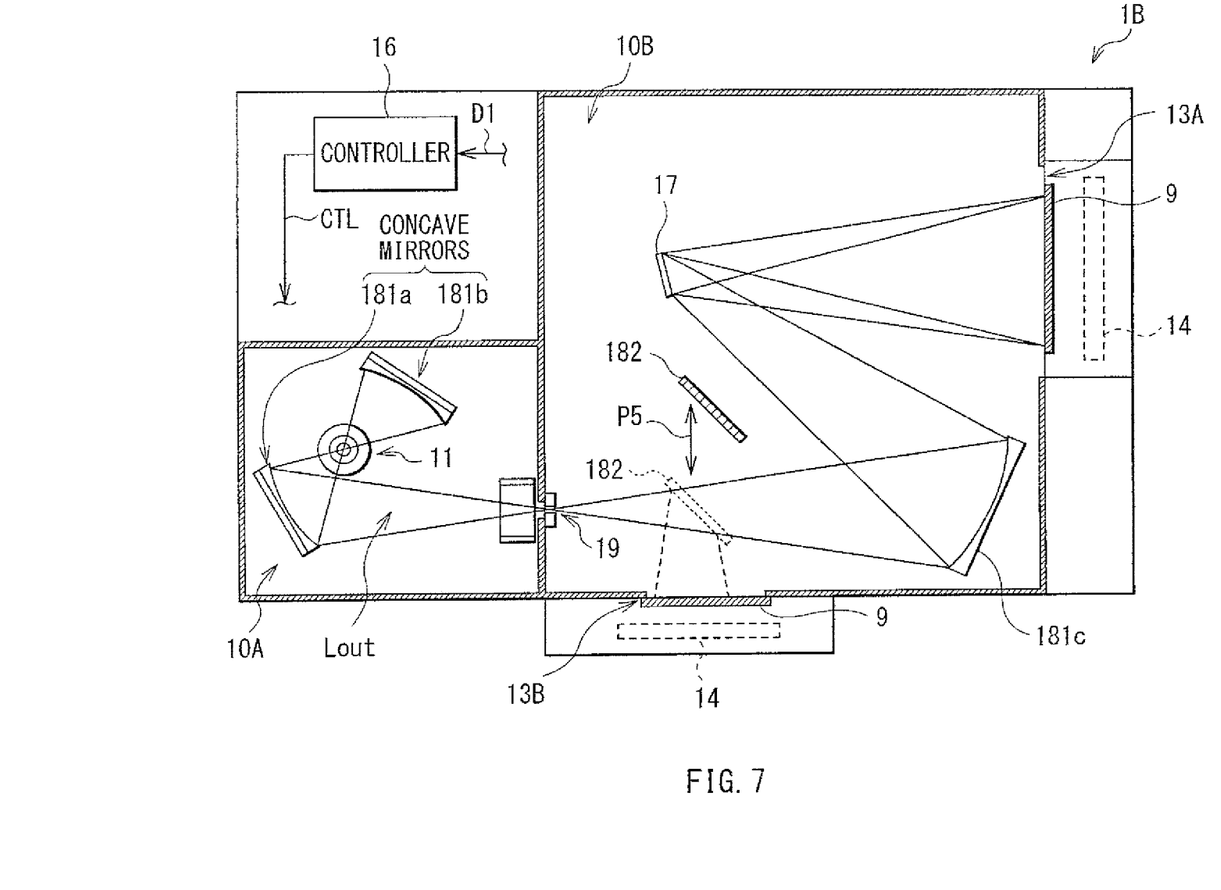
FIG. 7 schematically illustrates an example of an outline configuration of a weathering test instrument (a spectral aging test instrument) according to a second modification.

FIG. 7 schematically illustrates an example of an outline configuration of a weathering test instrument (a spectral aging test instrument) 1B according to a second modification. The spectral aging test instrument 1B may include the light source section 11, two sample holders 13A and 13B, three concave mirrors 181a, 181b, and 181c, a slit 19, a plane mirror 182, the diffraction grating 17, two light receptors 14, and the controller 16. Among these elements, the light source section 11 and the concave mirrors 181a and 181b are provided within a dark room 10A. Also, the slit 19, the plane mirror 182, the concave mirror 181c, and the diffraction grating 17 are provided within a dark room 10B. The light receptors 14 are disposed near the respective sample holders 13A and 13B to supply the pieces of light reception data D1 to the controller 16.

The concave mirrors 181a and 181b each serve to reflect the radiant light Lout emitted from the light source section 11 to guide the radiant light Lout from the inside of the dark room 10A to the dark room 10B through the slit 19.

The slit 19 is an opening that brings the dark rooms 10A and 10B into communication with each other, and is provided in an optical path of the radiant light Lout.

The plane mirror 182 is configured to reflect the radiant light Lout, and configured to be moved (displaced) as denoted by an arrow P5 in FIG. 7 in accordance with driving performed by an unillustrated driving section. For example, the plane mirror 182 is so configured as to be inserted to and removed from the optical path of the radiant light Lout and thus varied in position thereof as denoted by a solid line and a broken line in FIG. 7. Thus, when the plane mirror 182 is set at a position denoted by the solid line (the position off the optical path of the radiant light Lout), the radiant light Lout having entered through the slit 19 travels to the concave mirror 181c as it is without being reflected by the plane mirror 182. On the other hand, when the plane mirror 182 is set at a position denoted by the broken line (the position in the optical path of the radiant light Lout), the radiant light Lout having entered through the slit 19 is reflected by the plane mirror 182 to be guided to the sample holder 13B.

The concave mirror 181c serves to reflect the radiant light Lout having entered through the slit 19, and guide the radiant light Lout to the diffraction grating 17.

The diffraction grating 17 in this example may be configured to spectrally disperse the radiant light Lout having entered from the concave mirror 181c for each of the wavelength regions, and allow spectrally-dispersed radiant light (pieces of diffracted light) to exit therefrom to the sample holder 13A.

The present modification having the configuration described above allows for switchover of the optical path of the radiant light Lout in accordance with the positions (displacement operation) of the plane mirror 182. For example, the switchover may be made possible between guiding the radiant light Lout to the sample holder 13A without reflecting the radiant light Lout by the plane mirror 182 (former case) and guiding the radiant light Lout to the sample holder 13B by reflecting the radiant light Lout by the plane mirror 182 (latter case). In the former case, the sample 9 is fixed to the sample holder 13A and is irradiated with the radiant light Lout spectrally dispersed by the diffraction grating 17, whereby implementation of a spectral aging test such as that described in the foregoing first modification is made possible. In the latter case, the sample 9 is fixed to the sample holder 13B and is irradiated directly with the radiant light Lout that has not been subjected to interposition of the diffraction grating 17 (that has not been spectrally dispersed), whereby implementation of a regular weathering test is made possible. Hence, in the present modification, it is possible to implement a weathering test and a spectral aging test in one (single) apparatus using one (shared) light source section 11, by switching over from the weathering test to the spectral aging test and vice versa in the apparatus.

3. Other Modifications

Although the invention is described in the foregoing by way of example with reference to some example embodiments and modifications, the invention is not limited thereto but may be modified in a wide variety of ways.

For example, factors such as shapes, arranged positions, and the number of elements including the light source section, the sample-fixing frame, the sample holder, the light receptor, the light-receiving element, and the black panel thermometer are not limited to those described in the foregoing example embodiments and modifications, and any other shapes, arranged positions, and the number may be employed. For example, the annular sample-fixing frames may be of a fixed type (arranged to be fixed around the light source) instead of being those (of a rotation type) that perform the rotation operation around the light source. Also, the light source itself is also not limited to that of a fixed type. For example, the light source may be of a rotation type. In other words, the sample-fixing frames and the light source each may be of the fixed type or the rotation type, and such combinations constitute four types of embodiments (2×2=4 patterns) for the sample-fixing frames and the light source.

Also, factors such as shapes, arranged positions, and the number of elements including the light source packages and the solid-state light-emitting elements in the light source section are not limited to those described in the foregoing example embodiments and modifications as well, and any other shapes, arranged positions, and the number may be employed. For example, the light source packages 111 located in a circle around the base 110 may form a set, and a plurality of such sets of light source packages 111 may be provided on the base 110 in an extending direction (Z-axis direction) of the base 110. Also, for example, the plurality of solid-state light-emitting elements may be scattered over the base 110 to form the single light source package 111 as a whole. In such an embodiment, the solid-state light-emitting elements that emit respective light beams having different wavelength regions from one another may be mutually disposed in circle around the base 110, or may be disposed in the extending direction of the base 110, for example. Moreover, the number and kind of solid-state light-emitting elements included in the individual light source packages may be different for each of the light source packages, and each of the light source packages may be set to have any number of and/or any kind of solid-state light-emitting elements. For example, a visible light source package that includes one or more kinds of solid-state light-emitting elements that emit light in a visible region, an infrared light source package that includes one or more kinds of solid-state light-emitting elements that emit light in an infrared region, and an ultraviolet light source package that includes one or more kinds of solid-state light-emitting elements that emit light in an ultraviolet region may be provided separately, in one embodiment.

Further, although some example embodiments and modifications are described above giving LEDs and organic EL elements as examples of the solid-state light emitting elements, these are non-limiting examples and any other solid-state light emitting elements may be used. Examples of the solid-state light emitting elements may include, but not limited to, a light-emitting diode (LED), an organic electroluminescence (EL) element, a laser diode (LD), and any other suitable semiconductor light-emitting device.

In addition, although some example embodiments and modifications are described above with specific reference to various control operations performed by the controller and test methods, these are non-limiting examples and any other techniques may be employed to perform control operations and tests. For example, parameters other than the number of the solid-state light-emitting elements to emit the light, the emission intensity, and the emission time of the solid-state light-emitting elements may be controlled to control the radiant intensity (irradiance) for each of the wavelength regions. Also, the feedback control may be so performed as to maintain a spectral irradiance distribution other than the spectral irradiance distributions described in the foregoing example embodiments and modifications. Moreover, in one embodiment, control may be performed to stop operation of the entire weathering test instrument upon occurrence of failure (breakdown) or the like of a member (various members including the solid-state light-emitting elements) in the weathering test instrument, for example. In addition, for example, instead of individually receiving the radiant light for all of the wavelength regions from the light source section to perform the feedback control, a feedback control may be performed based on speculation without receiving radiant light in part of the wavelength regions, in one embodiment. More specifically, in one embodiment, a feedback control may be so performed that only the radiant light in a particular wavelength region is received and the entire spectral irradiance distribution, including wavelength regions other than the particular wavelength region, may be speculated based on the received light amount of the particular wavelength region. Further, in some cases, the light emission operation of the solid-state light-emitting elements may be performed without performing the feedback control.

Also, a method of sending the light reception data from the light receptor to the controller is not limited to that described in the foregoing example embodiments and modifications, and any other method may be used to send the data.

Further, the series of controls described in the foregoing example embodiments and modifications may be executed based on hardware (circuit) or software (program). In one embodiment where the controls are executed by software, the software may be configured by a program group that causes a computer (such as a microcomputer) to execute respective functions described above. Each program may be preinstalled in the computer, or may be installed into the computer from a network, a recording medium, or the like, for example.

Also, although some example embodiments and modifications are described above with reference examples where the solid-state light-emitting device system according to one embodiment of the invention is applied to a weathering test instrument or a spectral aging test instrument, these are non-limiting examples. The solid-state light-emitting device system according to one embodiment of the invention may be applied to any other apparatus or system. For example, the solid-state light-emitting device system according to one embodiment of the invention may be applied to a system such as a plant growth system, a disinfection system, a health promotion system, or the like.

Furthermore, the invention encompasses any possible combination of some or all of the various embodiments described herein and incorporated herein.

It is possible to achieve at least the following configurations from the above-described example embodiments of the invention.

(1) A weathering test instrument, including:
a light source section including a plurality of solid-state light-emitting elements, the solid-state light-emitting elements being different in kind from one another, and being configured to emit light beams having respective wavelength regions that are different from one another;
a light receptor configured to receive the light beams radiated from the light source section individually for the respective wavelength regions; and
a controller configured to control radiant intensities of the respective solid-state light-emitting elements individually, based on received light amounts for the respective wavelength regions derived from the light receptor, and thereby control irradiance at a sample surface for each of the wavelength regions to allow an accelerated test of a sample to be performed.

(2) The weathering test instrument according to (1), wherein the controller controls the radiant intensities of the respective solid-state light-emitting elements individually based on the received light amounts, to allow a spectral irradiance distribution set in the light source section to be maintained.

(3) The weathering test instrument according to (2), wherein the set spectral irradiance distribution is indicative of illuminance that is substantially same between the wavelength regions.

(4) The weathering test instrument according to (2), wherein the set spectral irradiance distribution is a distribution in which illuminance in each of the wavelength regions is larger than illuminance in each wavelength region in a spectral irradiance distribution of sunlight.

(5) The weathering test instrument according to (2), wherein the set spectral irradiance distribution is a distribution in which illuminance in an ultraviolet region is larger relatively than illuminance in any other wavelength region in the wavelength regions.

(6) The weathering test instrument according to any one of (1) to (5), wherein the light receptor includes:
one or more light-receiving elements; and
a plurality of wavelength-selective transmission filters provided on a light-receiving surface side of the one or more light-receiving elements, the wavelength-selective transmission filters being different in kind from one another, and being configured to allow the light beams radiated from the light source section to be transmitted therethrough individually for the respective wavelength regions.

(7) The weathering test instrument according to any one of (1) to (5), further including a diffraction grating configured to spectrally disperse the light beams radiated from the light source section for the respective wavelength regions,
wherein the light receptor receives the light beams spectrally dispersed by the diffraction grating to individually receive the light beams radiated from the light source section for the respective wavelength regions.

(8) The weathering test instrument according to any one of (1) to (7), wherein the controller controls one or more of: the number of the solid-state light-emitting elements to emit the light beams; an emission intensity of one or more of the solid-state light-emitting elements; and emission time of one or more of the solid-state light-emitting elements, to individually control the radiant intensities of the respective solid-state light-emitting elements.

(9) The weathering test instrument according to any one of (1) to (8), wherein each of the solid-state light-emitting elements is one of a light-emitting diode and an organic electroluminescence element.

(10) A solid-state light-emitting device system, including:
a light source section including a plurality of solid-state light-emitting elements, the solid-state light-emitting elements being different in kind from one another, and being configured to emit light beams having respective wavelength regions that are different from one another;
a light receptor configured to receive the light beams radiated from the light source section individually for the respective wavelength regions; and
a controller configured to control radiant intensities of the respective solid-state light-emitting elements individually, based on received light amounts for the respective wavelength regions derived from the light receptor, and thereby control irradiance at a sample surface for each of the wavelength regions to allow an accelerated test of a sample to be performed,
wherein the solid-state light-emitting device system is applied to a weathering test instrument.

Although the invention has been described in terms of exemplary embodiments, it is not limited thereto. It should be appreciated that variations may be made in the described embodiments by persons skilled in the art without departing from the scope of the invention as defined by the following claims. The limitations in the claims are to be interpreted broadly based on the language employed in the claims and not limited to examples described in this specification or during the prosecution of the application, and the examples are to be construed as non-exclusive. For example, in this disclosure, the term "preferably", "preferred" or the like is non-exclusive and means "preferably", but not limited to. The use of the terms first, second, etc. do not denote any order or importance, but rather the terms first, second, etc. are used to distinguish one element from another. Moreover, no element or component in this disclosure is intended to be dedicated to the public regardless of whether the element or component is explicitly recited in the following claims.

What is claimed is:

1. A weathering test instrument, comprising:
a light source section including a plurality of solid-state light-emitting elements, the solid-state light-emitting elements being different in kind from one another, and being configured to emit light beams having respective wavelength regions that are different from one another;
a light receptor including a plurality of light-receiving sensors configured to receive the light beams radiated from the light source section individually for the respective wavelength regions, each of the light-receiving sensors corresponding to a respective one of the solid-state light-emitting elements; and
a controller configured to control radiant intensities of the respective solid-state light-emitting elements individually, based on received light amounts for the respective wavelength regions derived from the light receptor to maintain a spectral irradiance distribution set in the light source section using feedback control based on the received light amounts to generate corresponding control signals for each of the solid-state light-emitting elements, and thereby control irradiance at a sample surface for each of the wavelength regions to allow an accelerated test of a sample to be performed.

2. The weathering test instrument according to claim 1, wherein the set spectral irradiance distribution is indicative of illuminance that is substantially same between the wavelength regions.

3. The weathering test instrument according to claim 1, wherein the set spectral irradiance distribution is a distribution in which illuminance in each of the wavelength regions is larger than illuminance in each wavelength region in a spectral irradiance distribution of sunlight.

4. The weathering test instrument according to claim 1, wherein the set spectral irradiance distribution is a distribution in which illuminance in an ultraviolet region is larger relatively than illuminance in any other wavelength region in the wavelength regions.

5. The weathering test instrument according to claim 1, wherein the light receptor comprises:
one or more light-receiving elements; and
a plurality of wavelength-selective transmission filters provided on a light-receiving surface side of the one or more light-receiving elements, the wavelength-selective transmission filters being different in kind from one another, and being configured to allow the light beams radiated from the light source section to be transmitted therethrough individually for the respective wavelength regions.

6. The weathering test instrument according to claim 1, further comprising a diffraction grating configured to spectrally disperse the light beams radiated from the light source section for the respective wavelength regions,
wherein the light receptor receives the light beams spectrally dispersed by the diffraction grating to individually receive the light beams radiated from the light source section for the respective wavelength regions.

7. The weathering test instrument according to claim 1, wherein the controller controls one or more of: the number of the solid-state light-emitting elements to emit the light beams; an emission intensity of one or more of the solid-state light-emitting elements; and emission time of one or more of the solid-state light-emitting elements, to individually control the radiant intensities of the respective solid-state light-emitting elements.

8. The weathering test instrument according to claim 1, wherein each of the solid-state light-emitting elements is one of a light-emitting diode and an organic electroluminescence element.

9. The weathering test instrument according to claim 1, further comprising:
a single sample holder configured to fix a sample in position; and
a diffraction grating configured to spectrally disperse the emitted light beams from the light source section for each of the wavelength regions to allow spectrally-disperse radiant light to exit therefrom to the sample,
wherein respective pieces of the spectrally dispersed radiant light are caused to be incident on the sample surface and the light receptor in order from a short wavelength to a long wavelength.

10. A solid-state light-emitting device system, comprising:
a light source section including a plurality of solid-state light-emitting elements, the solid-state light-emitting elements being different in kind from one another, and being configured to emit light beams having respective wavelength regions that are different from one another;

a light receptor including a plurality of light-receiving sensors configured to receive the light beams radiated from the light source section individually for the respective wavelength regions, each of the light-receiving sensors corresponding to a respective one of the solid-state light-emitting elements; and a controller configured to control radiant intensities of the respective solid-state light-emitting elements individually, based on received light amounts for the respective wavelength regions derived from the light receptor to maintain a spectral irradiance distribution set in the light source section using feedback control based on the received light elements, and thereby control irradiance at a sample surface for each of the wavelength regions to allow an accelerated test of a sample to be performed, wherein the solid-state light-emitting device system is applied to a weathering test instrument.

* * * * *